United States Patent [19]

Zeines

[11] Patent Number: 5,378,465
[45] Date of Patent: Jan. 3, 1995

[54] SOLUTION FOR APPLICATION TO AN ORAL CAVITY

[76] Inventor: Victor Zeines, P.O. Box 195 - Rt. 28, Shokan, N.Y. 12481

[21] Appl. No.: 66,784

[22] Filed: May 24, 1993

[51] Int. Cl.$^6$ .................. A61K 35/78; A61K 7/16; A61K 7/42

[52] U.S. Cl. .................. 424/195.1; 424/49; 424/58; 514/900; 514/901; 514/902

[58] Field of Search .................. 424/195.1, 49, 58

[56] References Cited

U.S. PATENT DOCUMENTS

| | | | |
|---|---|---|---|
| 4,376,115 | 3/1983 | McCrorey | 424/195.1 |
| 4,420,471 | 12/1983 | Elton et al. | 424/49 |
| 4,517,172 | 5/1985 | Southard | 424/195.1 |
| 5,072,368 | 12/1991 | Subramarian | 424/49 |

*Primary Examiner*—John W. Rollins
*Assistant Examiner*—Howard C. Lee
*Attorney, Agent, or Firm*—Schweitzer Cornman & Gross

[57] ABSTRACT

Described herein is an aqueous solution for application to an oral cavity generally as a mouthwash comprising an effective amount of echinacea, hydrastis canadensis, sanguinaria canadensis, quercus alba, grapefruit seed extract, aloe vera juice, water, vegetable glycerin, and peppermint oil.

4 Claims, No Drawings

SOLUTION FOR APPLICATION TO AN ORAL CAVITY

FIELD OF THE INVENTION

The invention relates to a solution for application to an oral cavity, particularly as a rinse such as a mouthwash.

BACKGROUND OF THE INVENTION

Statistics show that many people suffer from some form of gum (or periodontal) disease. Symptoms include puffy or bleeding gyms, bad breath, and eventually a loosening of the dentition.

Gum disease is defined as an infection of the supporting structures of the teeth. It occurs when the body is in a poor state of health as a result of digestive problems which may be due to an improper diet. Acid forming foods such as sugar, caffeine and meat may lead to a chemical imbalance in the mouth, which encourages bacteria to survive. The bacteria produce toxins which irritate and inflame the gum tissue. Eventually, the infection will progress to the point where it destroys the bone that supports the teeth.

THE INVENTION

It is an object of this invention to provide an aqueous solution for application to an oral cavity to treat such oral cavity.

A further object of this invention is to provide an aqueous solution for application to an oral cavity to promote general oral health.

Another object of this invention is to provide an aqueous solution for application to an oral cavity to treat swollen and bleeding gums.

Still another object of this invention is to provide an aqueous solution for application to an oral cavity to reduce plaque and help reduce tooth decay.

In its broadest sense, the present invention is directed to an aqueous solution for application to an oral cavity comprising an effective amount of the following ingredients:
 (a) echinacea;
 (b) hydrastis canadensis;
 (c) *Sanguinaria canadensis;*
 (d) quercus alba;
 (e) grapefruit seed extract;
 (t) aloe vera juice; and
 (g) calendula The echinacea, hydrastis canadensis, sanguinaria canadensis, quercus alba, and calendula re diluted with alcohol. The solution also may contain vegetable glycerin and peppermint oil.

The preferred embodiment of this invention is directed to an aqueous solution for application to an oral cavity comprising an effective amount of the following ingredients:
 (a) a combination of echinacea angustifola root, echinacea purpurea, and echinacea tennesiensis root;
 (b) hydrastis canadensis;
 (c) sanguinaria canadensis;
 (d) quercus alba;
 (e) grapefruit seed extract;
 (f) aloe vera juice;
 (g) calendula;
 (h) vegetable glycerin, and peppermint oil The echinacea, hydrastis canadensis, sanguinaria canadensis, quercus alba, and calendula are diluted with alcohol. The solution generally contains enough water to make one gallon of the mixture. The mixture is then diluted with an additional one to two gallons of water.

The echinacea, in its various forms, i.e., augustifolia and purpurea; hydrastis canadensis (goldenseal root); sanguinaria canadensis (bloodroot); quercus in its various forms including alba; aloe in its various forms including vera; and calendula in the form of calendula arvensis and calendula officinalis are well known herbs. These are particularly described in detail in Hortus Third, A Concise Dictionary, of Plants Cultivated in the United States and Canada, compiled by Bailey, et al., MacMillan Publishing Co., New York, 1976. However, the combination of these ingredients together with the vegetable glycerin and peppermint oil produces a synergistic effect to effectively help in healing puffy and/or bleeding gums, reducing bad breath, teeth decay and canker sore irritation.

The solution has been researched on about 100 patients with excellent results in helping to heal puffy and/or bleeding gums, reducing bad breath, teeth decay and canker sore irritation.

The solution is generally used as a mouthwash wherein the user rinses, for best results, with one capful of the bottled solution twice a day or more holding the solution in the mouth for about 20 to 30 seconds.

EXAMPLE

The following example serves to give specific illustration of the practice of this invention, but is not intended in any way to limit the scope of this invention.

Preparation of Solution

The following ingredients were combined:
 (a) 8 oz. of a combination of echinacea angustifola root, echinacea purpurea and echinacea tennesiensis root, 50% diluted with alcohol;
 (b) 4 oz. of hydrastis canadensis, 45% diluted with alcohol;
 (c) 4 oz. of sanguinaria canadensis 49% diluted with alcohol;
 (d) 4 oz. of quercus alba, 29% diluted with alcohol;
 (e) ¼ oz. of grapefruit seed extract;
 (f) 16 oz. of aloe vera juice;
 (g) ¼ oz. of calendula, 50% diluted with alcohol;
 (h) 16 oz. of vegetable glycerin;
 (i) 40 drops of peppermint oil; and
 (j) water in a quantity which makes one gallon of the mixture.

The solution as a mouthwash was used by about 100 patients experiencing one or more of puffy and/or bleeding gums, bad breath, teeth decay, and canker sore irritation. The use of the solution helped to cure and/or reduce these problems.

What is claimed is:

1. An aqueous solution for application to an oral cavity comprising an effective amount of the following ingredients combined in the ratio set forth:
 (a) approximately 8 oz. alcoholic echinacea tincture;
 (b) approximately 4 oz. alcoholic hydrastis canadensis tincture;
 (c) approximately 4 oz. alcoholic sanguinaria canadensis tincture;
 (d) approximately 4 oz. alcoholic quercus alba tincture;
 (e) approximately ¼ oz. grapefruit seed extract;

(f) approximately 16 oz. aloe vera juice;
(g) approximately ¼ oz. alcoholic calendula tincture; and
(h) water in an amount to make approximately one gallon of solution.

2. A solution as defined in claim 1 wherein the alcoholic echinacea tincture includes echinacea angustifola root, echinacea purpurea, and echinacea tennesiensis root diluted with alcohol.

3. A solution as defined in claim 2 which further includes approximately 16 oz. vegetable glycerin.

4. A solution as defined in claim 4, which further includes approximately 40 drops of peppermint oil.

* * * * *